United States Patent
Mai et al.

(10) Patent No.: US 9,746,441 B2
(45) Date of Patent: Aug. 29, 2017

(54) SENSOR, SENSOR KIT AND METHOD FOR DETECTING AN ANALYTE

(71) Applicant: Sony Corporation, Minato-ku (JP)

(72) Inventors: Michaela Mai, Stuttgart (DE);
Ingeborg Hospach, Winterlingen (DE);
Nadejda Krasteva, Fellbach (DE);
Gabriele Nelles, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 383 days.

(21) Appl. No.: 14/276,164

(22) Filed: May 13, 2014

(65) Prior Publication Data
US 2014/0332407 A1 Nov. 13, 2014

(30) Foreign Application Priority Data

May 13, 2013 (EP) .................................... 13167506

(51) Int. Cl.
*G01N 27/327* (2006.01)
*G01N 33/543* (2006.01)

(52) U.S. Cl.
CPC ..... *G01N 27/3276* (2013.01); *G01N 33/5438* (2013.01)

(58) Field of Classification Search
CPC ........... G01N 27/3275; G01N 27/3276; G01N 27/3277; C12Q 1/68; C12Q 1/6811; C12Q 1/6876; C12Q 1/6895; C12Q 2563/116; C12Q 2565/629; C12Q 2565/625

See application file for complete search history.

(56) References Cited

U.S. PATENT DOCUMENTS

| | | | | |
|---|---|---|---|---|
| 6,812,334 | B1* | 11/2004 | Mirkin | C12Q 1/6839 435/6.11 |
| 2003/0190608 | A1* | 10/2003 | Blackburn | B01J 19/0093 435/6.11 |
| 2010/0193378 | A1* | 8/2010 | Bratov | G01N 33/54306 205/792 |
| 2011/0042225 | A1* | 2/2011 | Adeloju | B82Y 15/00 205/170 |
| 2012/0220053 | A1* | 8/2012 | Lee | H01L 29/4908 436/501 |
| 2014/0106441 | A1* | 4/2014 | Wang | C12Q 1/689 435/287.2 |

OTHER PUBLICATIONS

Yosuke Amemiya et al., "Novel detection system for biomolecules using nano-sized bacterial magnetic particles and magnetic force microscopy", Journal of Biotechnology 120, 2005, 7 pages.
Eric Bakker et al., "Electrochemical Sensors", National Institutes of Health Public Access, Author Manuscript, Anal Chem 2006, 34 pages.
Leland C. Clark, Jr. et al., "Electrode Systems for Continuous Monitoring in Cardiovascular Surgery", Annals of the New York Academy of Sciences, vol. 102, No. 1, 1962, 17 pages.
Cornelius E. Knabbe et al., "Chip-based detection methods", Journal of Biophotonics, No. 4, 2009, 3 pages.

(Continued)

*Primary Examiner* — Gurpreet Kaur
(74) *Attorney, Agent, or Firm* — Oblon, McClelland, Maier & Neustadt, L.L.P.

(57) ABSTRACT

The present disclosure relates to electro-optical sensors, to sensor kits and methods for detecting an analyte in a sample.

13 Claims, 5 Drawing Sheets

A

B (56) References Cited

OTHER PUBLICATIONS

Won-Gun Koh, "Cell Microarrays Based on Hydrogel Microstructures for the Application to Cell-Based Biosensor", Biological Microarrays: Methods and Protocols, Methods in Molecular Biology, vol. 671, 2011, 13 pages.
Olivier Lazcka et al., "Pathogen detection: A perspective of traditional methods and biosensors", Biosensors and Bioelectronics 22, 2007, 13 pages.
A.Naebauer et al., "Biosensors Based on Piezoelectric Crystals", Sensors and Actuators, B1, 1990, 2 pages.
Thomas Schueler et al., "A disposable and cost efficient microfluidic device for the rapid chip-based electrical detection of DNA", Biosensors and Bioelectronics 25, 2009, 7 pages.
Marie-Bernadette Villiers et al. "Peptide-protein microarrays and surface plasmon resonance detection: Biosensors for versatile biomolecular interaction analysis", Biosensors and Bioelectronics 26, 2010, 6 pages.
Joseph Wang, "Glucose Biosensors: 40 years of Advances and Challenges", Electroanalysis, 2001, 6 pages.
Herbert Wiesinger-Mayr et al., "Identification of human pathogens isolated from blood using microarray hybridisation and signal pattern recognition", BMC Microbiology, 2007, 17 pages.

* cited by examiner

SENSOR, SENSOR KIT AND METHOD FOR DETECTING AN ANALYTE

BACKGROUND

The present disclosure relates to electro-optical sensors, to sensor kits and methods for detecting an analyte in a sample.

The analysis of bimolecular interactions plays an important role in medical applications for disease progression, prognosis and prevention. Specific biomolecule interactions (e.g. induced fit) can be used in healthcare (biosensors, biochips, lab-on-a-chip) and lifestyle applications (mood sensors) or for sensing environmental changes (ecological sensors) or as military devices (sensors for biological weapons and warfare agents).

In all these cases, a miniaturization of the device in combination with a multiplexing capacity and simple sample handling for small sample volumes is needed and summed up under the keywords "point-of-care" and "point-of need" application. Another desirable feature of, e.g., biochips is fast and reliable sample readout. Most applications reported or developed in this area are based on either optical readout with fluorescence (e.g. microarrays) or electrochemical readout (e.g. blood-glucose tests), both comprising several advantages and disadvantages.

One of the first biosensors for medical application was published in 1962, dealing with the development of a glucose sensor based on glucose oxidase [1]. Nowadays, chip-based detection methods for medical diagnosis are still of special interest in an emerging research field [2]. In general, biosensors consist of three relevant elements: a bio-molecular recognition element, a signal transducer and the signal readout system. They are based on substrates like glass, polymers, cellulose membranes to name but a few. As bio-molecular recognition element, enzymes [3], DNA [4], cells [5] and antibodies [6] may be used. The signal can be transduced by mechanical means, by optical means or by electrical means. Dependent on the transducer, several readout methods for bio-sensing devices are known and published. Among them are optical sensors [7] (e.g. fluorescence, luminescence and plasmonics), electrochemical sensors [7], [8] (e.g. amperometric and potentiometric sensors), magnetic bead sensors [9] and piezoelectric sensors [10]. Silver enhancement may be used for electrical readout of the signal for DNA detection [11].

SUMMARY

However, for fast, highly specific and sensitive diagnosis systems with a large dynamic range, further development and an advanced technology are needed which will help to pass from research field to the diagnostic application area. More particularly, there is a need for highly sensitive sensors, which are able to detect biomolecule interactions. A biosensor should be a fast, sensitive and specific device without the need of pre-concentration of the analyte to be detected. For advanced sensor applications, e.g. in the fields of non-invasive medical diagnosis, environmental monitoring, food quality control, etc., the specific and selective detection of small and large amounts of biomolecules which are known as, e.g., molecular markers for diseases, degradation processes in food, or environmental pollution, is necessary. In these cases, a low detection limit (in the pg/ml to ng/ml concentration range) as well as a broad dynamic range of the detection system is needed.

It was an object to provide a sensor or sensor system that has the above properties. It was another object to provide a method for detecting an analyte using such sensor or sensor system.

The objects are solved by a sensor comprising
  a substrate,
  an electrode structure comprising at least two electrodes, said electrode structure being deposited on said substrate, and
  a plurality of analyte-specific primary receptor molecules immobilized on a surface of said substrate in a gap between said at least two electrodes.

In one embodiment, said substrate is a solid substrate. In one embodiment, said substrate is of a material selected from the group consisting of inorganic materials, organic materials and combinations thereof. In one embodiment, said inorganic materials are selected from the group consisting of glass, silicon (Si) and silicon dioxide ($SiO_2$). In one embodiment, said organic materials are selected from the group consisting of synthetic polymers or co-polymers, naturally occurring polymers (e.g. cellulose) and transparent carbon-based materials. In one embodiment, said substrate is a layered structure comprising inorganic (e.g. glass) and organic (e.g. polymer) material.

In one embodiment, said glass is selected from the group consisting of borosilicate glass (e.g. BK7), transparent conductive oxide coated glass (TCO) (e.g. ITO-coated glass, FTO-coated glass, AZO-coated glass, ATO-coated glass), lime-soda glass, LaSF glass, silica glass and optical crown glass. In one embodiment, said synthetic polymers or co-polymers are selected from the group consisting of acrylates, such as polymethylmetacrylate (PMMA), polyethylene (PE), polypropylene, cyclic olefin polymer (COP), polyurethane (PU), polystyrene (PS), polyether ether ketone (PEEK), polyimide and polyethylene terephthalate (PETP).

In one embodiment, said surface is chemically modified, preferably chemically modified with a plurality of linker molecules allowing the immobilization of said primary receptor molecules. In one embodiment, said surface is silanized, preferably by using silanes with functional groups such as carboxy groups, amine groups, quaternary ammonium groups, thiol groups, halogens and epoxy groups. Preferred linker molecules are, e.g., bissulfosuccinimidyl suberate ($BS_3$) and linker molecules based on PEG. In general, all types of zero-length crosslinkers (carbodiimides, EDC), homobifunctional crosslinkers, heterobifunctional crosslinkers or trifunctional crosslinkers can be used as linker molecules.

In one embodiment, said surface is chemically modified with a three-dimensional structure allowing the immobilization of said primary receptor molecules, preferably between said at least two electrodes, thereby reducing unspecific immobilization of the primary receptor molecules.

In one embodiment, said three-dimensional structure is a hydrogel, e.g. based on synthetic polymers and natural polymers (e.g. collagen) containing terminal functional groups allowing binding of the primary receptor molecules, e.g. NHS-ester groups, epoxy groups, carboxyl groups or amine groups.

In one embodiment, said three-dimensional structure is a nanoparticle film, preferably metal (e.g. Au) nanoparticle film, or a porous thin metal (e.g. Au) film. Preferably, said nanoparticle film is porous. In one embodiment, said porous thin metal film has a thickness of 1 to 500 nm, preferably 1 to 50 nm.

In one embodiment, said porous thin metal film is deposited onto said substrate supported by an adhesive layer of Cr or Ti having a thickness of 1-2 nm. In one embodiment, said nanoparticle film is deposited onto said substrate, wherein said substrate is decorated with linker molecules (e.g. amino silanes or epoxy silanes). In one embodiment, said nanoparticle film is deposited directly onto said substrate without using linker molecules or an adhesive layer.

In one embodiment, said electrode structure is of a material selected from the group consisting of conductive metals (e.g. Au, Ti, Ag, Cu, Pt, Al), conductive metal oxides (e.g. ITO, FTO), conductive polymers (e.g. PEDOT-PSS, polypyrrole, polythiophene, polyaniline) and semi-conductive materials (InSb, $SnO_2$, $TiO_2$).

In one embodiment, said electrode structure is an interdigitated microelectrode, wherein, preferably, said interdigitated microelectrode has a finger gap in the range of 1 nm to 5 μm, more preferably an interdigitated microelectrode with intervals between 500 nm to 1 μm and 1 nm to 100 nm.

In one embodiment, said sensor further comprises contact pads connected to said at least two electrodes.

In one embodiment, said sensor is a biosensor.

In one embodiment, said primary receptor molecules are selected from the group consisting of proteins, peptides, antibodies, affibodies, Fab-fragments, enzymes, DNA (e.g. cDNA or DNA primers), RNA (e.g. mRNA, siRNA or miRNA), lipids, carbohydrates, microorganisms and cells.

In one embodiment, said sensor further comprises said analyte bound to said primary receptor molecules.

In one embodiment, reactive species on said surface (e.g. unreacted functional groups of linker molecules) are blocked by treatment with a suitable blocking solution (e.g. a buffered solution, e.g. PBS, comprising PEG or proteins, such as bovine serum albumin and casein).

In one embodiment, said sensor further comprises an analyte-specific secondary receptor molecule bound to said analyte, wherein said secondary receptor molecule is different from said primary receptor molecules and comprises at least one electrically conductive or semi-conductive label or an enzyme promoting the deposition of metal atoms or of at least one electrically conductive or semi-conductive label.

In one embodiment, said at least one electrically conductive or semi-conductive label is selected from the group consisting of metal nanoparticles and quantum dots.

In one embodiment, said secondary receptor molecule further comprises an electrically non-conductive label, e.g. an organic or inorganic (fluorescent) dye or an enzyme promoting the deposition of a non-conductive label.

In one embodiment, said enzyme promoting the deposition of metal atoms is a peroxidase, preferably horseradish peroxidase (HRP). In one embodiment, said metal atoms are silver or gold atoms.

In one embodiment, said sensor further comprises an additional conductive layer in said gap between said at least two electrodes, which is deposited by means of a chemical or an enzymatic reaction.

The objects are also solved by a sensor kit comprising a sensor as defined above and
an analyte-specific secondary receptor molecule, wherein said secondary receptor molecule is different from said primary receptor molecules and comprises at least one electrically conductive or semi-conductive label or an enzyme promoting the deposition of metal atoms or of at least one electrically conductive or semi-conductive label.

In one embodiment, said at least one electrically conductive or semi-conductive label is selected from the group consisting of metal nanoparticles and quantum dots.

In one embodiment, said secondary receptor molecule further comprises an electrically non-conductive label, e.g. an organic or inorganic (fluorescent) dye or an enzyme promoting the deposition of a non-conductive label.

In one embodiment, said enzyme promoting the deposition of metal atoms is a peroxidase, preferably horseradish peroxidase (HRP).

In one embodiment, said sensor kit further comprises a solution of metal ions.

In one embodiment, said metal atoms are silver atoms, and said metal ions are silver ions, or said metal atoms are gold atoms, and said metal ions are gold ions.

The objects are also solved by the use of a sensor as defined above or of a sensor kit as defined above for detecting an analyte in a sample.

The objects are also solved by a method for detecting an analyte in a sample, said method comprising the steps of:
(a) providing a sensor as defined above;
(b) measuring at least one electrical property and, optionally, at least one optical property of said gap between said at least two electrodes;
(c) exposing said sensor to said sample;
(d) exposing said sensor to an analyte-specific secondary receptor molecule, wherein said secondary receptor molecule is different from said primary receptor molecules and comprises at least one electrically conductive or semi-conductive label or an enzyme promoting the deposition of metal atoms or of at least one electrically conductive or semi-conductive label,
wherein, when said secondary receptor molecule comprises an enzyme promoting the deposition of metal atoms or of at least one electrically conductive or semi-conductive label, said sensor is further exposed to a solution of metal ions or a solution of at least one electrically conductive or semi-conductive label; and
(e) measuring said at least one electrical property and, optionally, said at least one optical property of said gap between said at least two electrodes,
wherein a difference between at least one electrical property and, optionally, said at least one optical property measured in step (b) and said at least one electrical property and, optionally, said at least one optical property measured in step (e) indicates the presence of said analyte in said sample.

In one embodiment, said at least one electrically conductive or semi-conductive label is selected from the group consisting of metal nanoparticles and quantum dots.

In one embodiment, said secondary receptor molecule further comprises an electrically non-conductive label, e.g. an organic or inorganic (fluorescent) dye or an enzyme promoting the deposition of a non-conductive label.

In one embodiment, said enzyme promoting the deposition of metal atoms is a peroxidase, preferably horseradish peroxidase (HRP).

In one embodiment, said metal atoms are silver atoms, and said metal ions are silver ions, or said metal atoms are gold atoms, and said metal ions are gold ions.

In one embodiment, said electrical property is measured by using direct current or alternating current. In one embodiment, said electrical property is selected from the group consisting of resistance, conductance, impedance and capacitance.

In one embodiment, said optical property is selected from the group consisting of surface plasmon resonance, transmittance, reflection, absorption, luminescence, phosphorescence and fluorescence.

In one embodiment, said method further comprises the step of depositing an additional conductive layer in said gap between said at least two electrodes, wherein said step is performed after step (d) and before step (e), and wherein said step is performed by means of a physical, chemical or an enzymatic reaction.

The objects are also solved by a method for producing a sensor as defined above, said method comprising the steps of
(a) providing a substrate as defined above;
(b) depositing an electrode structure as defined above comprising at least two electrodes on said substrate; and
(c) immobilizing a plurality of analyte-specific primary receptor molecules as defined above on a surface of said substrate in a gap between said at least two electrodes.

In one embodiment, said method further comprises the step of cleaning said substrate, wherein said step is performed after step (b) and before step (c).

In one embodiment, said method further comprises the step of activating said surface as defined above and/or the step of chemically modifying said surface as defined above and/or the step of depositing a three-dimensional structure as defined above on said surface as defined above, wherein any of these steps is performed after step (b) (and after said optional step of cleaning said substrate) and before step (c).

In one embodiment, said method further comprises the step of depositing an additional nanoparticle layer onto said substrate, e.g. a self-assembled monolayer (SAM) of nanoparticles, in particular metal (e.g. Au) nanoparticles.

In one embodiment, said method further comprises the step of blocking reactive species on said surface, e.g. by treatment with a blocking solution (e.g. a solution of BSA), wherein said step is performed after step (c).

The term "nanoparticles", as used herein, refers to particles having a size in the range of 0.1 to 1000 nm, preferably 0.1 to 500 nm, more preferably 0.1 to 50 nm. The nanoparticles according to the present disclosure may have rod-shape ("nanorods"), disk shape (platelets) and/or spherical shape.

The sensor system in accordance with the present disclosure is based on the combination of an optical readout and an electrochemical readout, termed electro-optical readout, by the deposition of conductive material between sensor structures. The detection of the bimolecular interaction can be realized electrically by measuring impedance, conductance, resistance or capacity changes in the conductive material deposited between two electrode structures. In addition to the change in electrical properties, the deposition of conductive material (e.g. metal particles) can be visualized and analysed optically by transmittance, absorption, reflection and/or localized surface plasmon resonance (LSPR) measurements.

An electrical chip according to the present disclosure is small, robust and easy to integrate in mobile devices for point-of-need application. Optical readout is flexible, specific and sensitive in a large dynamic range. The advantage of the combination of both electrical and optical readout is a high capacity for multiplexing with high flexibility and precision due to internal control with different measurement techniques. High-throughput capacities and automation in sample application and readout can also be realized in a setup which is compatible to all body fluids. The use of 3D substrates modified by a hydrogel or (nanoparticle) films will contribute to highly sensitive and specific sensors.

The main advantages of the sensor system in accordance with the present disclosure are based on its high flexibility due to the combined readout systems:
multiple analysis on one single sensor is possible by spatial resolution;
the integration with gas-sensing is possible, and different sources of samples can be analysed;
a combination of electrical and optical detection allows signal to noise (S/N) and signal to background (S/B) ratio control;
the generation of a signal due to metal deposition—from zero resistance (or plasmon band (PB) absorbance) to measurable resistance (or PB absorbance)—allows a binary ON/OFF response;
signal enhancement is achieved due to metal generation/deposition;
Au on Au and Ag on Au will produce different absorbance, but probably similar resistance change; and
enzyme activity can be measured and controlled by concomitant fluorescence.

BRIEF DESCRIPTION OF THE DRAWINGS

Reference is now made to the figures, wherein.

DETAILED DESCRIPTION

The present disclosure is further described by means of the following examples, which are meant to illustrate the present disclosure, but not to limit it.
Sensor Layout and Principle Mechanism of Analyte Detection (e.g. Detection of an Antigen)

Figure 1:
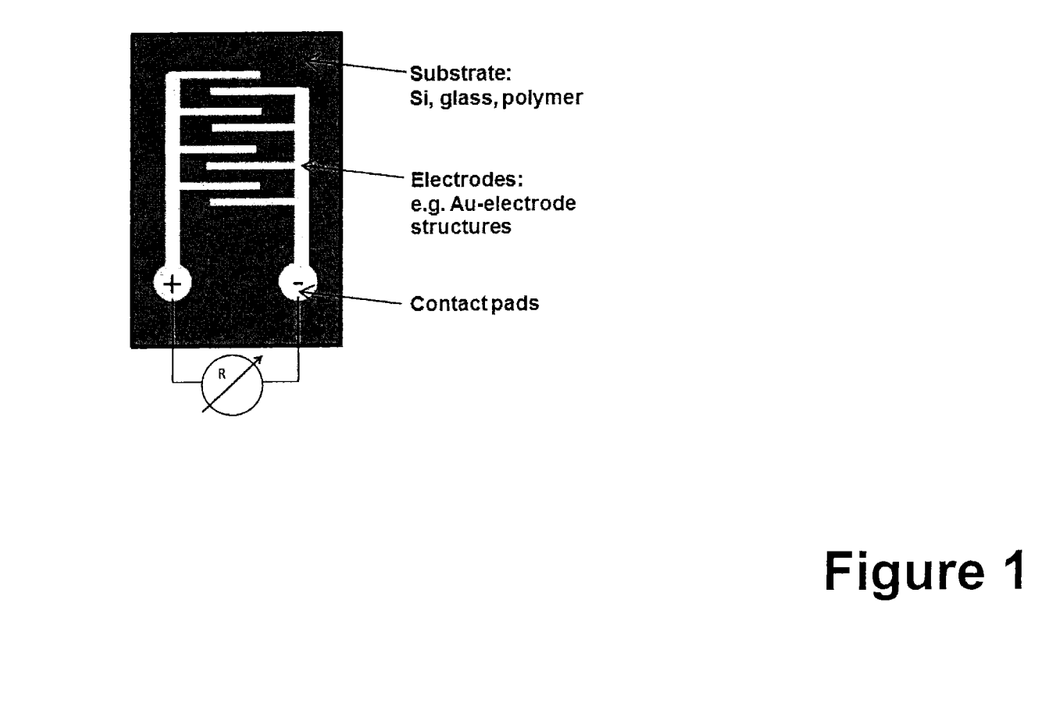
FIG. 1 is a schematical representation of a sensor in accordance with the present disclosure (seen from top) consisting of a sensor substrate, interdigitated electrode structures and contact pads.

An exemplary sensor in accordance with the present disclosure comprises interdigitated gold-electrode structures defined on a substrate (FIG. 1). This sensor allows an electro-optical detection of molecule interactions (e.g. antibody (AB)/antigen (AG) binding) by measuring a change of electrical properties (resistance, conductance, impedance and/or capacitance) and/or optical properties (UV/Vis, fluorescence, localized surface plasmon resonance—LSPR) of a biological sensitive layer. Receptor or capture probes can be either proteins, antibodies, affibodies, Fab-fragments, peptides, enzymes, DNA, RNA, lipids, carbohydrates, microorganisms or cells. Besides metallic nanoparticles, quantum dots, organic and inorganic dyes can be used as labels. In the following, TNF-α (as AG), anti-TNF-α antibodies (as AB) and the metals silver and gold are used as a model system.

Sensor Structure and Composition

Figure 2:
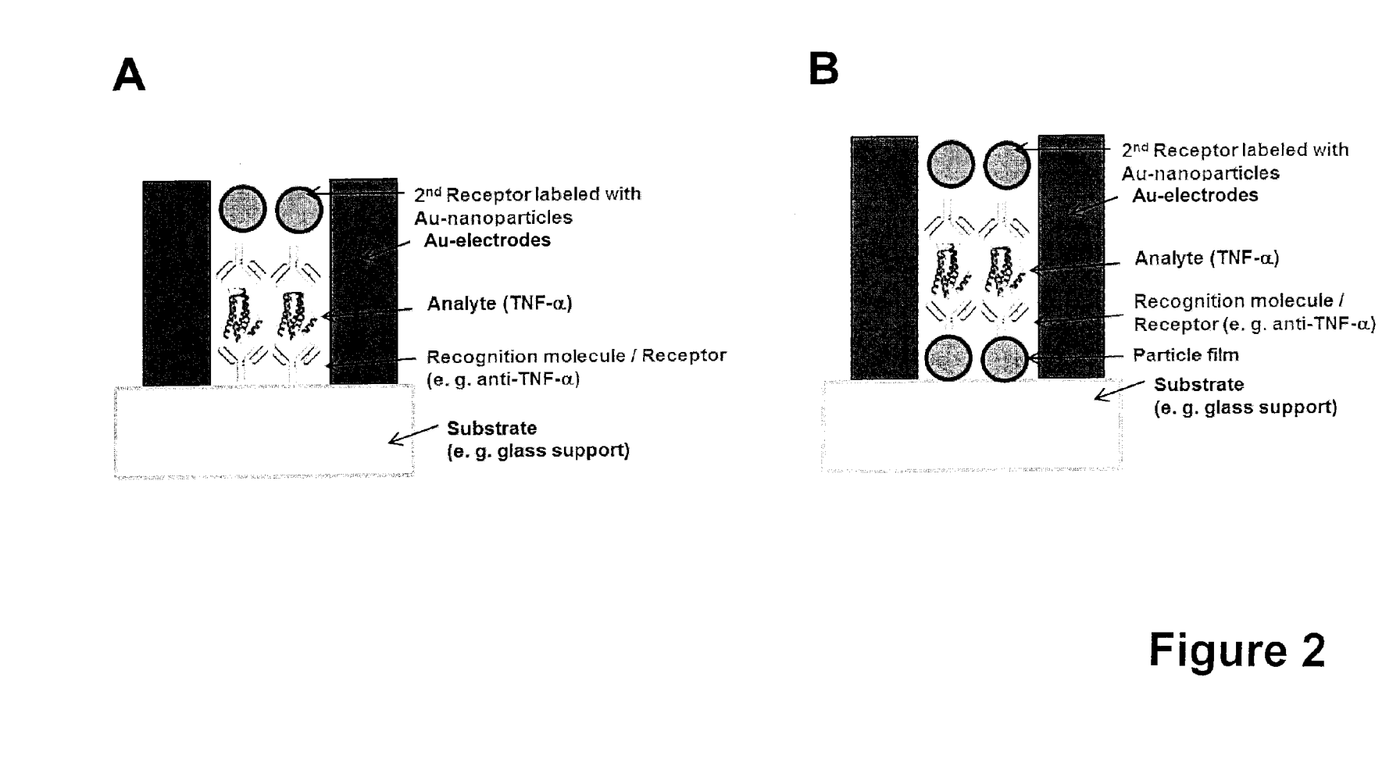
FIG. 2 shows two possible sensor structures in accordance with the present disclosure, setup model I (A) and model II (B)

Two possible sensor structures are depicted in FIG. 2. The principle idea is to immobilize receptor molecules as recognition elements (e.g. a primary AB) either directly on the surface of a chemically modified (e.g. silane) substrate (e.g. glass, Si, polymer) or on a substrate modified with a 3D structure (e.g. a hydrogel) (A). Another option is the attachment of recognition elements on the surface of a porous metal nanoparticle film or porous metal film which is pre-deposited on the chemically modified substrate (B).

As next step, a liquid or gaseous sample containing analytes or molecules of interest for detection (e.g. an AG) is brought in contact with the sensor, and the analytes are captured by the immobilized primary receptor molecules. Subsequently, a labeled secondary receptor molecule functioning as a detection molecule (e.g. a secondary AB) is provided to the sensor. This secondary receptor can bind to the sensor only if the AG has already interacted with the primary receptor molecule. Due to a specific label (e.g. Au-nanoparticles) of the detection molecule, the sensor response can be measured via electro-optical methods. Exemplary process protocols for models I and II (cf. FIG. 2) are given in Table 1.

layers. A combination of, e.g., Au and Ag nanoparticles will shift the initial plasmon from Au-wavelength to a mixed wavelength to a Ag-wavelength when Ag is sequentially deposited on the Au particles, and vice versa. The application of different metals and shapes as labels for different secondary AB for the diverse antigens allows multiplex analysis on the same chip.

The combination of both readout techniques allows a parallel, fast and reliable measurement. For example, one can detect binding of the analyte via electrical readout and optically on the space free of electrodes. Alternatively, one can account for non-specific binding by measuring LSPR on the space free of electrodes. Further, fluorescence readout can be additionally used. For a fast and simple sample application, a microfluidic setup is considered.

Signal Enhancement

Figure 3:
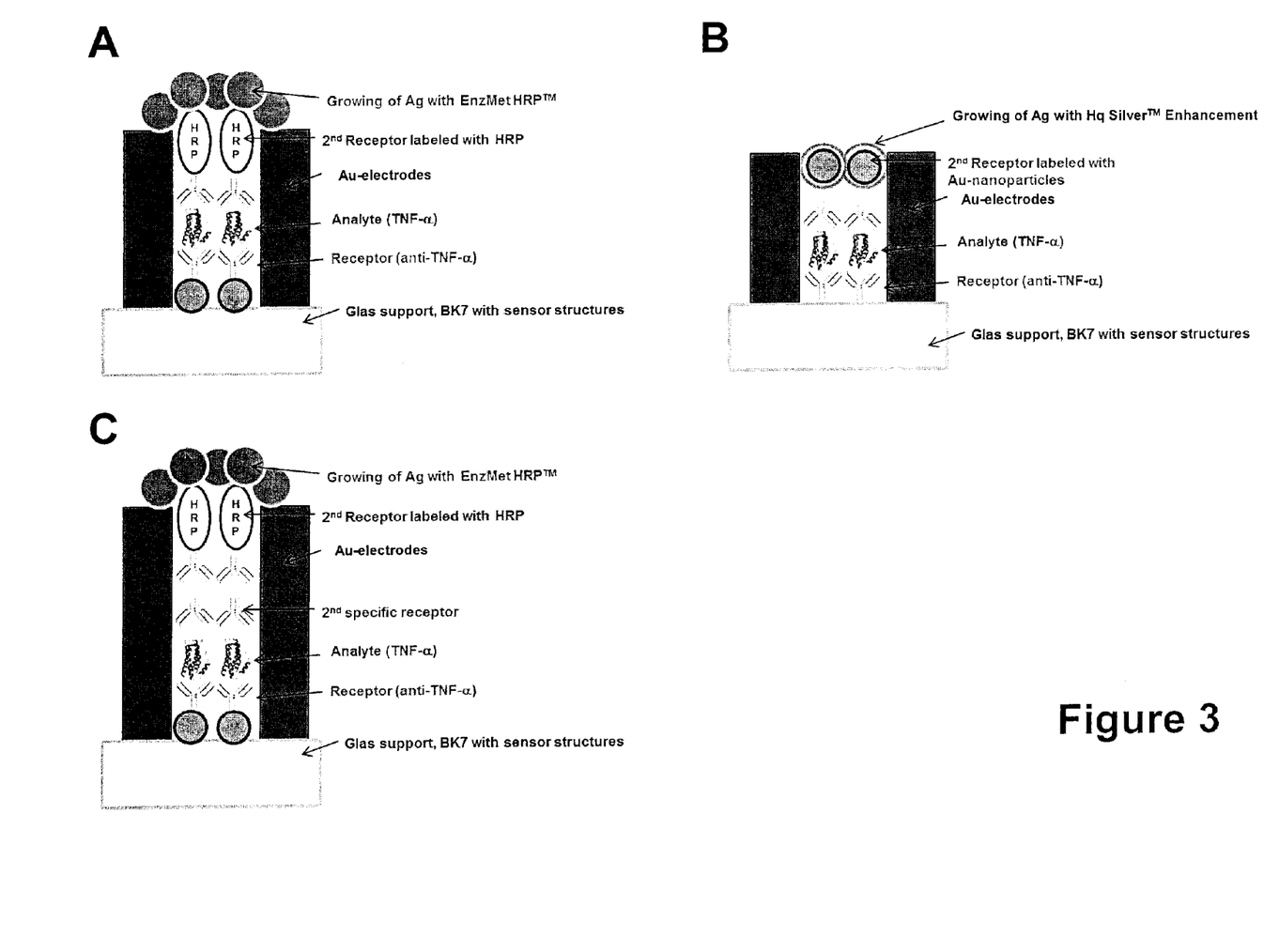
FIG. 3 illustrates readout methods with silver enhancement based on the models depicted in FIG. 2, wherein the methods depicted in A and C use the EnzMet™ kit (Nanoprobes, USA) with enzymatic catalysis of insoluble silver deposition and the method depicted in B uses Hq Sliver™ enhancement (Nanoprobes, USA) for growing a silver shell around Au nanoparticles.
Figure 4:
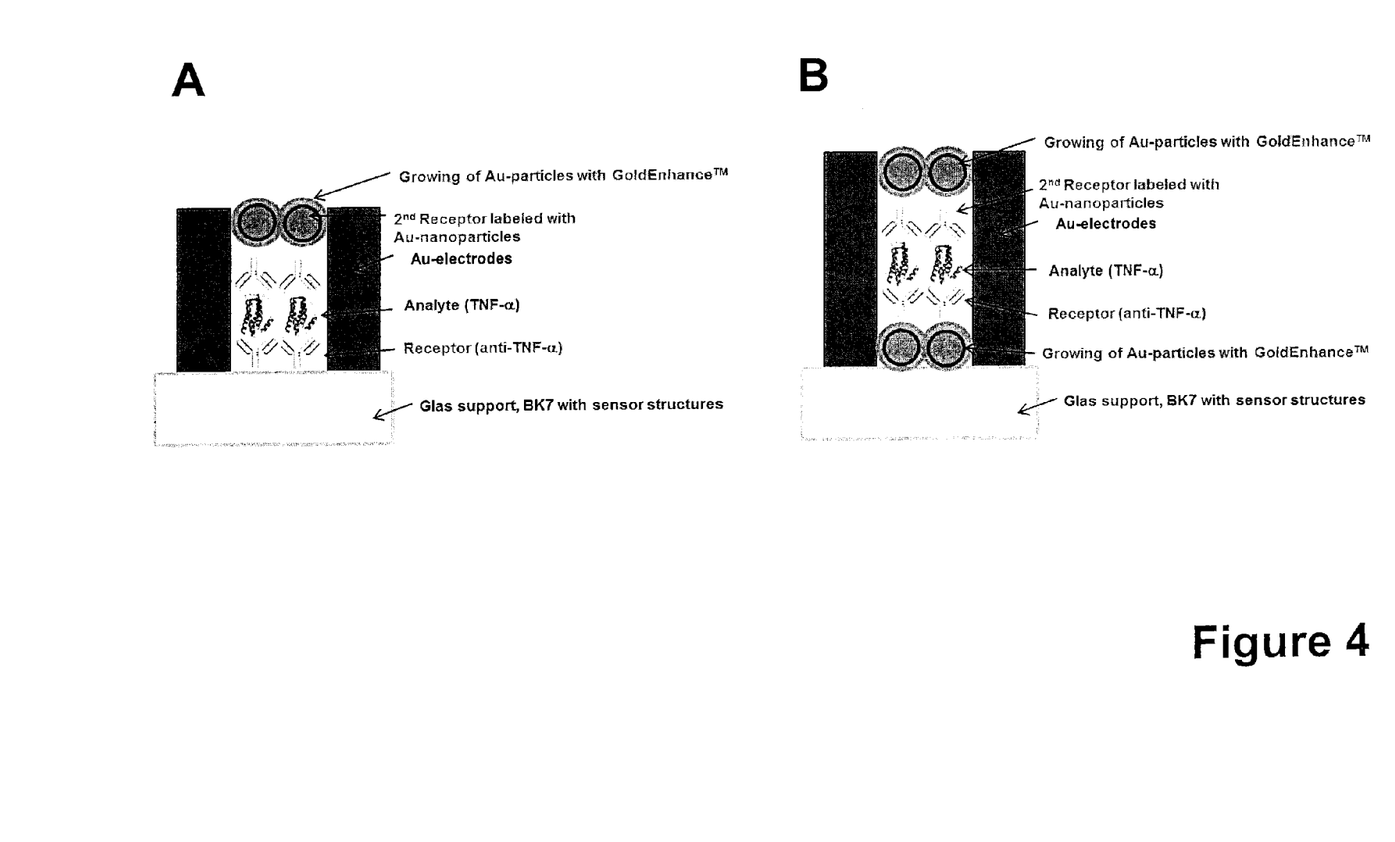
FIG. 4 illustrates two methods with gold enhancement (GoldEnhance™, Nanoprobes, USA) based on the models depicted in FIG. 2.
Figure 5:
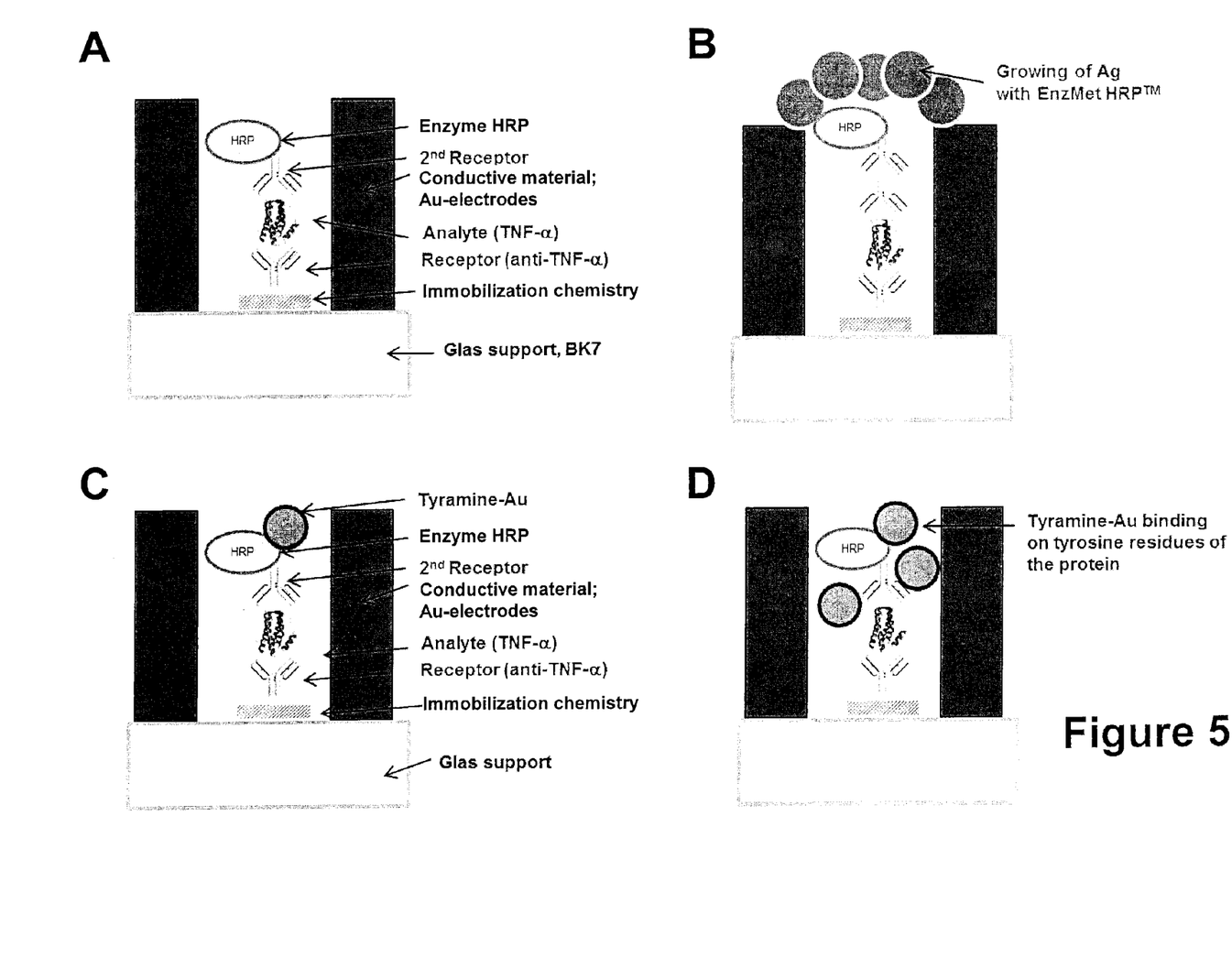
FIG. 5 illustrates the readout method using HRP for the reduction of silver ions (A/B; EnzMetHRP™) or for catalyzing the binding of tyramine-labeled Au nanoparticles to tyrosine residues of the second receptor (C/D).

An enhancement of the sensor signal can be achieved by the additional deposition of a conductive layer, e.g. a layer of metal nanoparticles, such as silver or gold nanoparticles, using a chemical or an enzymatic reaction [11], supported by, e.g., an EnzMetHRP™ kit, GoldEnhance™, Hq Silver™ enhancement kit (Nanoprobes, USA) or tyramine labeled metal particles. The principle of this enhancement is described in the following and is depicted in FIGS. 3 and 5 B (for silver) and FIGS. 4 and 5 C/D (for gold).

TABLE 1

Exemplary protocols for sensor models I and II (cf. FIG. 2).

| Protocol for model I: | Protocol for model II: |
|---|---|
| Support: e.g. BK7 substrate with large sensor structures for proof of principle (pop) | Support: e.g. BK7 substrate with large sensor structures for proof of principle (pop) |
| Cleaning of substrate | Cleaning of substrate |
| Surface activation and/or coating with immobilization chemistry (e.g. silanization; linker molecules e.g. EDC/NHS coupling, bissulfo-succinimidylsuberate ($BS_3$) or covalent coupling of His-tagged proteins using a 3D structure, e.g. hydrogel) | Surface activation and/or coating with immobilization chemistry (e.g. silanization; linker molecules e.g. EDC/NHS coupling, bissulfo-succinimidylsuberate ($BS_3$) or covalent coupling of His-tagged proteins using a 3D structure, e.g. hydrogel) |
| Binding of $1^{st}$ receptor | SAM of nanoparticle film/metal nanoparticles/nanostructures (e.g. Au) |
| Blocking of reactive species on the surface (e.g. with BSA) | Binding of $1^{st}$ receptor |
| Application of analyte sample | Blocking of reactive species on the surface (e.g. with BSA) |
| Analyte detection (verification with LSPR possible, dependent on area) | Application of analyte sample |
| $2^{nd}$ labeled receptor for signal enhancement and electrical readout (see below): | Analyte detection (verification with LSPR possible, dependent on area) |
| AB-Streptavidin-HRP → silver deposition | $2^{nd}$ labeled receptor for signal enhancement (see below): |
| Gold labeled receptor → gold deposition | AB-Streptavidin-HRP → silver deposition |
| | Gold labeled receptor → gold deposition |

Electro-Optical Readout

The sensor described can be used for

1.) electrical detection and/or

2.) optical detection

Ad. 1.) The specific binding of the secondary receptor might be detected by a change of resistance, conductance, impedance and/or capacitance of the sensor when the detection receptor, which is labeled with Au-nanoparticles or with other nanoparticles of various shapes, is applied (see FIG. 2). The readout by resistivity measurements might be integrated easily in chemical gas sensing devices. This fast readout may be performed online in a microfluidic setup.

Ad. 2.) The specific molecular interaction with the secondary AB can also be detected optically, e.g. by measuring the plasmon shift upon deposition of additional particle Silver Enhancement:

Silver ions will be reduced to elementary silver through catalytic reactions with enzymes called peroxidases. These enzymes are ubiquitous in nature, very stable and have broad substrate spectra. Well characterized is the peroxidase from horse radish (HRP), which can be either linked directly to the specific secondary AB (FIG. 3 A) or indirectly to a less specific secondary AB (FIG. 3 C). The silver product generated will be insoluble and will enhance the signal of both the electrical and optical readout. Furthermore, LSPR spectra of gold and silver-particles or the mixture of gold and silver-particles can be recorded and used to differentiate between receptor binding and analyte binding. A further possibility is the use of the Hq Sliver kit (Nanoprobes, USA) for the growth of silver on Au-nanoparticles (FIG. 3 B). The fluorescence generated by the silver-HRP-complex can be used for fluorescence enhancement or quenching detection systems [12].

Gold Enhancement:

Gold particles may grow chemically with GoldEnhance™ (Nanoprobes, USA), which occurs in the dark and unspecifically labels the particles and enhances the signal of both the optical and electrical readout.

The sensitivity of the sensor system according to the present disclosure is given by the quality of AB-AG binding and by the amount of nanoparticles which label the secondary AB. High loading of receptors on a 3D structured surfaces (e.g. hydrogel, membrane etc.) will intensify the signal. Selectivity of the sensor system is given by the specificity of the biomolecules and the affinity of the specific induced fit mechanism.

The features disclosed in the specification, the claims, and/or in the accompanying drawings may, both separately and in any combination thereof, be material for realizing the disclosure in various forms thereof.

The present disclosure is also described by means of the following embodiments:

Embodiment 1

Sensor comprising
a substrate,
an electrode structure comprising at least two electrodes, said electrode structure being deposited on said substrate, and
a plurality of analyte-specific primary receptor molecules immobilized on a surface of said substrate in a gap between said at least two electrodes.

Embodiment 2

Sensor according to embodiment 1, wherein said substrate is of a material selected from the group consisting of inorganic materials, organic materials and combinations thereof.

Embodiment 3

Sensor according to embodiment 1 or 2, wherein said surface is chemically modified, preferably chemically modified with a plurality of linker molecules allowing the immobilization of said primary receptor molecules.

Embodiment 4

Sensor according to any of embodiments 1 to 3, wherein said surface is chemically modified with a three-dimensional structure allowing the immobilization of said primary receptor molecules.

Embodiment 5

Sensor according to embodiment 4, wherein said three-dimensional structure is a hydrogel.

Embodiment 6

Sensor according to embodiment 4, wherein said three-dimensional structure is a nanoparticle film, preferably metal nanoparticle film, or a porous metal film.

Embodiment 7

Sensor according to any of embodiments 1 to 6, wherein said electrode structure is of a material selected from the group consisting of conductive metals, conductive metal oxides, conductive polymers and semi-conductive materials.

Embodiment 8

Sensor according to any of embodiments 1 to 7, wherein said electrode structure is an interdigitated microelectrode, preferably an interdigitated microelectrode with a finger gap in the range of 1 nm to 5 μm, more preferably an interdigitated microelectrode with intervals between 500 nm to 1 μm and 1 nm to 100 nm.

Embodiment 9

Sensor according to any of embodiments 1 to 8, wherein said primary receptor molecules are selected from the group consisting of proteins, peptides, antibodies, affibodies, Fab-fragments, enzymes, DNA, RNA, lipids, carbohydrates, microorganisms and cells.

Embodiment 10

Sensor according to any of embodiments 1 to 9, further comprising an analyte bound to said primary receptor molecules.

Embodiment 11

Sensor according to embodiment 10, further comprising an analyte-specific secondary receptor molecule bound to said analyte, wherein said secondary receptor molecule is different from said primary receptor molecules and comprises at least one electrically conductive or semi-conductive label or an enzyme promoting the deposition of metal atoms or of at least one electrically conductive or semi-conductive label.

Embodiment 12

Sensor according to embodiment 11, wherein said at least one electrically conductive or semi-conductive label is selected from the group consisting of metal nanoparticles and quantum dots.

Embodiment 13

Sensor according to embodiment 11, wherein said enzyme promoting the deposition of metal atoms is a peroxidase, preferably horseradish peroxidase (HRP).

Embodiment 14

Sensor according to any of embodiments 11 to 13, further comprising an additional conductive layer in said gap between said at least two electrodes, which is deposited by means of a chemical or an enzymatic reaction.

Embodiment 15

Sensor kit comprising
a sensor according to any of embodiments 1 to 9 and
an analyte-specific secondary receptor molecule, wherein said secondary receptor molecule is different from said primary receptor molecules and comprises at least one electrically conductive or semi-conductive label or an enzyme promoting the deposition of metal atoms or of at least one electrically conductive or semi-conductive label.

Embodiment 16

Sensor kit according to embodiment 15, wherein said at least one electrically conductive or semi-conductive label is selected from the group consisting of metal nanoparticles and quantum dots.

Embodiment 17

Sensor kit according to embodiment 15, wherein said enzyme promoting the deposition of metal atoms is a peroxidase, preferably horseradish peroxidase (HRP).

Embodiment 18

Sensor kit according to any of embodiments 15 to 17, further comprising a solution of metal ions.

Embodiment 19

Use of a sensor according to any of embodiments 1 to 9 or of a sensor kit according to any of embodiments 15 to 18 for detecting an analyte in a sample.

Embodiment 20

Method for detecting an analyte in a sample, said method comprising the steps of:
(a) providing a sensor according to any of embodiments 1 to 9;
(b) measuring at least one electrical property and, optionally, at least one optical property of said gap between said at least two electrodes;
(c) exposing said sensor to said sample;
(d) exposing said sensor to an analyte-specific secondary receptor molecule, wherein said secondary receptor molecule is different from said primary receptor molecules and comprises at least one electrically conductive or semi-conductive label or an enzyme promoting the deposition of metal atoms or of at least one electrically conductive or semi-conductive label,
wherein, when said secondary receptor molecule comprises an enzyme promoting the deposition of metal atoms or of at least one electrically conductive or semi-conductive label, said sensor is further exposed to a solution of metal ions or a solution of at least one electrically conductive or semi-conductive label; and
(e) measuring said at least one electrical property and, optionally, said at least one optical property of said gap between said at least two electrodes,
wherein a difference between at least one electrical property and, optionally, said at least one optical property measured in step (b) and said at least one electrical property and, optionally, said at least one optical property measured in step (e) indicates the presence of said analyte in said sample.

Embodiment 21

Method according to embodiment 20, wherein said at least one electrically conductive or semi-conductive label is selected from the group consisting of metal nanoparticles and quantum dots.

Embodiment 22

Method according to embodiment 20, wherein said enzyme promoting the deposition of metal atoms is a peroxidase, preferably horseradish peroxidase (HRP).

Embodiment 23

Method according to any of embodiments 20 to 22, wherein said electrical property is selected from the group consisting of resistance, conductance, impedance and capacitance.

Embodiment 24

Method according to any of embodiments 20 to 23, wherein said optical property is selected from the group consisting of surface plasmon resonance, transmittance, reflection, absorption, luminescence, phosphorescence and fluorescence.

Embodiment 25

Method according to any of embodiments 20 to 24, further comprising the step of depositing an additional conductive layer in said gap between said at least two electrodes, wherein said step is performed after step (d) and before step (e), and wherein said step is performed by means of a physical, chemical or an enzymatic reaction.

The present application claims priority to European Patent Application 13 167 506.8, filed in the European Patent Office on May 13, 2013, the entire contents of which being incorporated herein by reference.

REFERENCES

[1] C. L. L. C. Clark Jr., "Electrode systems for continuous monitoring in cardiovascular surgery," Ann. NY Acad. Sci, p. 29-45, 1962.
[2] C. K. et al., "Chip-based detection methods," Biophotonics, vol. 2, no. 4, p. 193-195, 2009.
[3] J. Wang, "Glucose Biosensors: 40 Years of Advances," Electroanalysis, vol. 13, no. 12, pp. 1040-0397/01/1208-0983, 2000.
[4] Herbert Wiesinger-Mayr et al. "Identification of human pathogens isolated from blood using microarray hybridisation and signal pattern recognition," BMC Microbiology, vol. 78, no. 7, pp. 10.1186/1471-2180-7-78, 2007.
[5] W.-G. Koh, "Cell Microarrays Based on Hydrogel Microstructures for the Application to Cell-Based Biosensor," Methods in Molecular Biology, Vols. Volume 671, Part 1, 133-145, DOI: 10.1007/978-1-59745-551-0_7, no. Part 1, pp. 10.1007/978-1-59745-551-0_7, 2011.
[6] M.-B. V. et al., "Peptide-protein microarrays and surface plasmon resonance detection," Biosensors and Bioelectronics, vol. 26, p. 1554-1559, 2010.
[7] O. Lazcka, "Pathogen detection: A perspective of traditional methods and biosensors," Biosensors and Bioelectronics, vol. 22, p. 1205-1217, 2007.
[8] E. Bakker, "Electrochemical Sensors," Analytical Chemistry, vol. 78, no. 12, p. 3965-3984, 2006.
[9] Y. Amemiya, "Novel detection system for biomolecules using nano-sized bacterial magnetic particles and magnetic force microscopy," Journal of Biotechnology, vol. 120, no. 3, p. 308-314, 2005.

[10] A. Näbauer, "Biosensors based on piezoelectric crystals," Sensors and Actuators B: Chemical, vol. 1, no. 1-6, p. 508-509, 1990.

[11] T. Schüler, "A disposable and cost efficient microfluidic device for the rapid chip-based electrical detection of DNA," Biosensors and Bioelectronics, vol. 25, no. 1, p. 15-21, 2009.

[12] Wen et al., "Horseradish peroxidase functionalized fluorescent gold nanoclusters for hydrogen peroxide sensing." Analytical Chemistry, vol. 83, no. 4, p. 1193-1196, 2011.

The invention claimed is:

1. A sensor, comprising
    a substrate;
    an electrode structure comprising at least two electrodes, said electrode structure being deposited on said substrate; and
    a plurality of analyte-specific primary receptor molecules immobilized on a surface of said substrate in a gap between said at least two electrodes,
    wherein said surface is chemically modified with a three-dimensional nanoparticle film for the immobilization of said analyte-specific primary receptor molecules, and
    wherein said nanoparticle film is directly attached to said substrate without a linker molecule.

2. The sensor of claim 1, wherein said substrate is of a material selected from the group consisting of inorganic materials, organic materials, and combinations thereof.

3. The sensor of claim 1, wherein said nanoparticle film is porous and has a thickness of 1-50 nm.

4. The sensor of claim 1, wherein said electrode structure is of a material selected from the group consisting of conductive metals, conductive metal oxides, conductive polymers, and semi-conductive materials.

5. The sensor of claim 1, wherein said electrode structure is an interdigitated microelectrode with intervals between 500 nm to 1 µm and 1 nm to 100 nm.

6. The sensor of claim 1, wherein said analyte-specific primary receptor molecules are selected from the group consisting of proteins, peptides, antibodies, affibodies, Fab-fragments, enzymes, DNA, RNA, lipids, carbohydrates, microorganisms, and cells.

7. The sensor of claim 1, further comprising:
    an analyte bound to said analyte-specific primary receptor molecules.

8. The sensor of claim 7, further comprising:
    an analyte-specific secondary receptor molecule bound to said analyte,
    wherein said analyte-specific secondary receptor molecule is different from said analyte-specific primary receptor molecules and comprises at least one electrically conductive or semi-conductive label or an enzyme promoting the deposition of metal atoms or of at least one electrically conductive or semi-conductive label.

9. The sensor of claim 8, wherein said at least one electrically conductive or semi-conductive label is selected from the group consisting of metal nanoparticles and quantum dots.

10. The sensor of claim 8, wherein said enzyme promoting the deposition of metal atoms is a peroxidase.

11. The sensor of claim 8, further comprising:
    an additional conductive layer in said gap between said at least two electrodes, which is deposited by means of a chemical or an enzymatic reaction.

12. A sensor kit, comprising:
    a sensor according to claim 1; and
    an analyte-specific secondary receptor molecule, wherein said analyte-specific secondary receptor molecule is different from said analyte-specific primary receptor molecules and comprises at least one electrically conductive or semi-conductive label or an enzyme promoting the deposition of metal atoms or of at least one electrically conductive or semi-conductive label.

13. A method for detecting an analyte in a sample, said method comprising:
    (a) providing a sensor according to claim 1;
    (b) measuring at least one electrical property and, optionally, at least one optical property of said gap between said at least two electrodes;
    (c) exposing said sensor to said sample;
    (d) exposing said sensor to an analyte-specific secondary receptor molecule, wherein said analyte-specific secondary receptor molecule is different from said analyte-specific primary receptor molecules and comprises at least one electrically conductive or semi-conductive label or an enzyme promoting the deposition of metal atoms or of at least one electrically conductive or semi-conductive label,
    wherein, when said analyte-specific secondary receptor molecule comprises an enzyme promoting the deposition of metal atoms or of at least one electrically conductive or semi-conductive label, said sensor is further exposed to a solution of metal ions or a solution of at least one electrically conductive or semi-conductive label; and
    (e) measuring said at least one electrical property and, optionally, said at least one optical property of said gap between said at least two electrodes,
    wherein a difference between at least one electrical property and, optionally, said at least one optical property measured in (b) and said at least one electrical property and, optionally, said at least one optical property measured in (e) indicates the presence of said analyte in said sample.

* * * * *